United States Patent
Huggins (10) Patent No.: US 11,577,048 B2
(45) Date of Patent: Feb. 14, 2023

(54) MEDICAL DEVICE BENDING TOOL

(71) Applicant: Argon Medical Devices, Inc., Frisco, TX (US)

(72) Inventor: Brandon Huggins, Chicago, IL (US)

(73) Assignee: Argon Medical Devices, Inc., Frisco, TX (US)

(*) Notice: Subject to any disclaimer, the term of this patent is extended or adjusted under 35 U.S.C. 154(b) by 1020 days.

(21) Appl. No.: 16/290,726

(22) Filed: Mar. 1, 2019

(65) Prior Publication Data
US 2020/0276409 A1    Sep. 3, 2020

(51) Int. Cl.
*A61B 17/34* (2006.01)
*A61M 25/00* (2006.01)
(Continued)

(52) U.S. Cl.
CPC ..... *A61M 25/0054* (2013.01); *A61B 17/3421* (2013.01); *A61M 25/0009* (2013.01); *A61M 25/0041* (2013.01); *A61M 25/0662* (2013.01); *A61M 27/002* (2013.01); *A61B 2017/00526* (2013.01); *A61B 2017/568* (2013.01); *A61M 2025/0063* (2013.01)

(58) Field of Classification Search
CPC . B21G 1/08; B21G 1/00; B21G 1/003; B21G 1/006; B21G 1/02; B21G 1/06; B21F 1/00; B21F 1/006; B21F 1/008; B21F 1/004; B21F 1/002; B21D 7/02; B21D 7/024; B21D 7/04; A61M 2025/0036; A61B 2017/00526; A61B 2017/568; A61B 17/3421
See application file for complete search history.

(56) References Cited

U.S. PATENT DOCUMENTS

| 166,294 | A | 3/1875 | Orum |
| 406,992 | A | 7/1889 | Burgoin |

(Continued)

FOREIGN PATENT DOCUMENTS

| CN | 2287228 | 8/1998 |
| CN | 102189201 | 9/2011 |

(Continued)

OTHER PUBLICATIONS

5-Piece Spring Type Tupe Bender Set—Item # 60360 by Micro-Mark; URL: https://www.micromark.com/5-piece-Spring-Type-Tube-Bender-Set.

*Primary Examiner* — Majid Jamialahmadi
(74) *Attorney, Agent, or Firm* — IpHorgan Ltd.

(57) ABSTRACT

A method and system of bending medical device components for customization to a particular medical procedure and patient while generally maintaining the ideal performance of the component. A medical professional embeds the medical device component into a bending tool. The medical professional then aligns an intended curve region of the medical device component within a bending region of the bending tool and imparts a curve in the bending region. Finally, the medical professional withdraws the medical device component from the bending tool, and utilizes the bent medical device component in the medical procedure. The system may be a kit comprising various medical device components for a particular medical procedure and a suitable bending tool for those components.

14 Claims, 7 Drawing Sheets

(51) Int. Cl.
*A61B 17/00* (2006.01)
*A61B 17/56* (2006.01)
*A61M 25/06* (2006.01)
*A61M 27/00* (2006.01)

(56) References Cited

U.S. PATENT DOCUMENTS

| | | |
|---|---|---|
| 411,756 A | 9/1889 | Brigham |
| 539,378 A | 5/1895 | Bropson |
| 1,675,574 A | 7/1928 | Mykins |
| 2,041,428 A | 5/1936 | Milligan |
| 2,760,545 A | 8/1956 | Solemslie |
| 5,106,381 A | 4/1992 | Chikama |
| 5,176,126 A | 1/1993 | Chikama |
| 5,201,210 A * | 4/1993 | Stein, III ............... A61M 5/32 72/457 |
| 5,363,882 A | 11/1994 | Chikama |
| 5,954,672 A | 9/1999 | Schwager |
| 8,287,496 B2 | 10/2012 | Racz |
| 9,901,705 B2 | 2/2018 | Armour et al. |
| 2004/0258789 A1 | 12/2004 | Phillips |

FOREIGN PATENT DOCUMENTS

| | | |
|---|---|---|
| CN | 202462871 | 10/2012 |
| CN | 203391302 | 1/2014 |
| CN | 204866965 | 12/2015 |
| EP | 1149640 | 10/2001 |
| EP | 3318343 | 5/2018 |
| GB | 195278 | 3/1923 |
| JP | 11-221853 | 8/1999 |
| KR | 20100136851 | 12/2010 |

\* cited by examiner

MEDICAL DEVICE BENDING TOOL

BACKGROUND

Technical Field

This application relates to a bending tool for use with medical devices and more particularly to a bending tool for use with needles, cannulas, catheters, and the like.

Background of Related Art

Medical devices often require customization for each specific patent and procedure, such as catheters, needles or cannulas. This customization is often performed by a medical professional immediately preceding or during a procedure, where saving time and ensuring accuracy is essential.

For example, in endovascular procedures, a medical professional needs to adapt said procedure to a particular patient and her layout of blood vessels. Considering the delicate and intricate nature of performing medical procedures intravenously, it is paramount any medical device is configured properly. A proper configuration ensures the device will reach the desired procedure site while causing as little trauma to the preceding vessels as possible.

More specifically, a medical professional may have to modify a medical device for the insertion of a transjugular intrahepatic portosystemic shunt ("TIPS"). A TIPS is used to treat portal hypertension-high blood pressure in veins inside and surrounding the liver. Various liver diseases, such as cirrhosis, reduce blood flow through the liver, resulting in a pressure buildup in the portal veins preceding the liver. This increased pressure can have negative consequences, such as internal bleeding and accumulation of fluids. A TIPS procedure inserts a shunt inside a preselected branch of the incoming portal vein to the outgoing hepatic vein, thus allowing some blood to bypass the liver and relieving the hypertension. The TIPS procedure is performed through the jugular vein using specially designed catheters and needles.

A medical professional begins a TIPS procedure by inserting a catheter into a patient's jugular vein and, with the help of x-ray imaging, guides the catheter toward one of the liver's hepatic veins. A TIPS needle is advanced down the catheter into the hepatic vein. This needle is sometimes curved to better facilitate placement of the needle during the procedure. The needle punctures the hepatic vein, travels through the liver and into the portal vein. A guidewire is inserted through the needle to maintain access to the area as the needle is removed. A balloon is advanced down the guidewire into the liver and inflated, creating a tract. A vascular sheath is advanced down the guidewire and into the tract. Finally a stent is inserted into the sheath to maintain its size and shape. Further details of the TIPS procedure is described in U.S. Pat. No. 8,632,468.

As it is impractical for manufactures to preemptively produce custom sized and shaped medical devices for each procedure and patient, such as a TIPS procedure, a medical professional must modify a medical device near the time of or during a medical procedure. Thus, it is important for a medical professional to be able to quickly and effectively modify medical devices during medical procedures. Unfortunately, such modifications can sometimes negatively impact the performance of the device. For example, in some instances, it may be desired to introduce a desired angle in a needle to enhance the ability to negotiate the tortuous path to the procedure site or to better control the needle function at the procedure site. However, often this may result in a deformation in the cross sectional shape of the needle which may reduce or even eliminate entirely the fluid flow through the needle. Such bending may also introduce "kinks" in the needle which can increase the difficulty to advance the needle through a vein or cause trauma to the vein. Thus, a solution is required which allows for end user bending and modification of medical devices which maintains the performance and/or integrity of the device.

SUMMARY

The present invention provides a method of bending a medical device component for use in a contemporaneous or shortly succeeding medical procedure, the method comprising: inserting a medical device component into a bending tool, bending the bending tool and the medical device component, removing the medical device component from the bending tool, and utilizing the bent medical device component in a medical procedure.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

Figure 1:
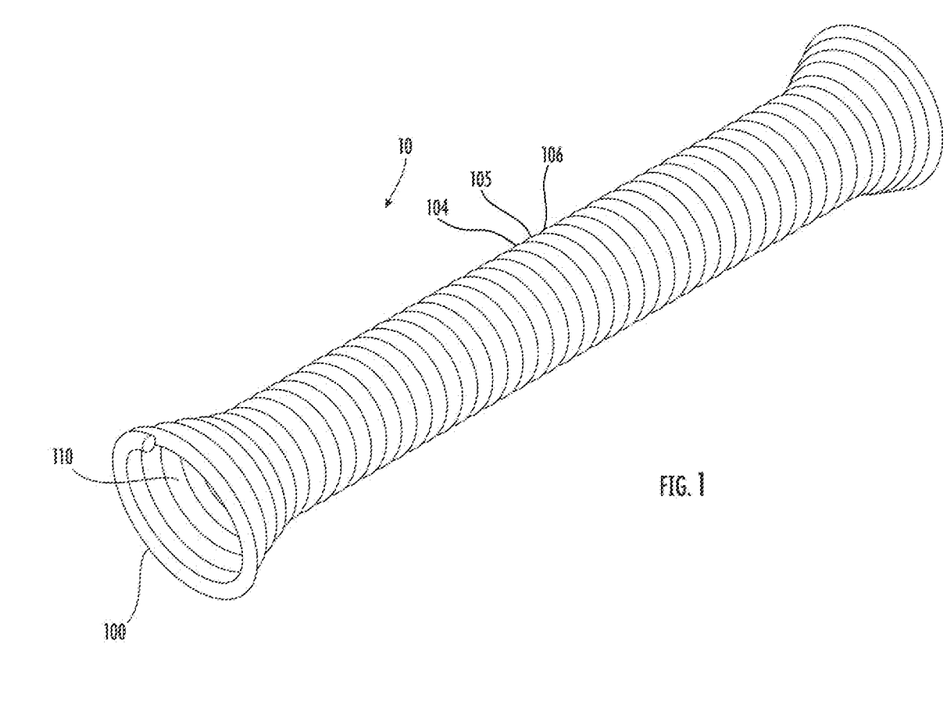
FIG. 1 is an isometric view of a bending tool.

FIG. 1 shows an isometric view of bending tool 10. Bending tool 10 may be made from a wire 100 spun in a helical shape to form a cylinder-like shape. The wire may form repeating circles which generally abut their neighboring circles, such that bending tool 10 may stretch or bend, but may not substantially compress. Three representative adjacent circles are shown as 104, 105, and 106. The generally abutting circles form inner surface 110.

The wire or rod material may be steel, stainless steel, aluminum, other metals both ferrous and non-ferrous, or alloys of the aforementioned materials. Wire 100 may be designed with various cross-section shapes, such as circular, oval, square, rectangular, or the like. The thickness of wire 100 may range from about 32 American Wire Gauge ("AWG") to about 14 AWG, preferably about 30 AWG to about 18 AWG, and most preferably, about 27 AWG to about 19 AWG. Bending tool 10 may undergo tumble finishing or other finishing process to deburr and smooth the tool.

Figure 2:
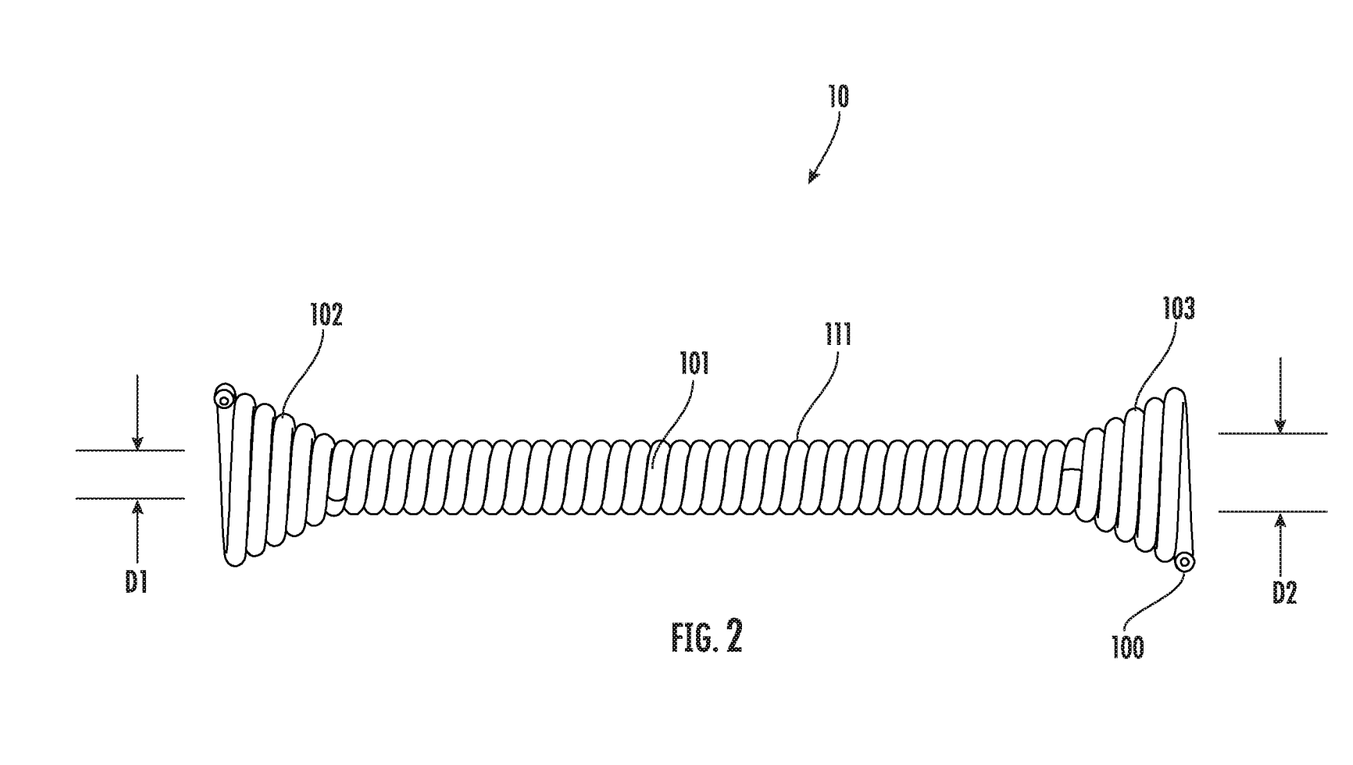
FIG. 2 is an orthogonal view of the bending tool of FIG. 1.

As shown in FIG. 2, bending tool 10 may comprise three regions: bending region 101, flared insertion region or first end 102 and flared insertion region or second end 103. Wire 100 forms exterior surface 111 and interior surface 110. Exterior surface 111 along bending region 101 provides an outer diameter which may vary between minimum and maximum along the longest axis due to the high and low points formed by wire 100, if it has a round cross section. Similarly, interior surface 110 provides an inside diameter which varies between a minimum and maximum. Inside diameter D1 refers to the minimum diameter while outer diameter D2 refers to the maximum diameter.

Inner diameter D1 of bending tool 10 within bending region 101 may range from about 0.006 to about 0.2 inches, preferably between about 0.03 and about 0.18 inches, and most preferably between about 0.05 to about 0.16 inches. Bending region 101 may be designed with inner diameter D1 identical to or slightly larger than an outer diameter of an object which requires bending, such as a surgical needle, cannula, dilator, trocar stylet, or other medical device components. In one embodiment, inner diameter D1 of bending tool 10 is adapted to fit over a 14 gauge (Birmingham Gauge) blunt-end cannula. In another embodiment, the inner diameter of bending tool is adapted to fit over a 16 gauge hypodermic needle.

Referring again to FIG. 2, bending tool 10 may have flared insertion regions 102 and 103. Bending tool 10 may include no insertion region, one, or both. Each flared insertion region may be located at each far end of bending tool 10. Flared insertion region 102 or 103 may be integrated into the shape formed by wire 100 beginning at the bending region 101. Either flared insertion region may generally form a conical frustum-like shape, wherein the top of the conical frustum abuts bending region 101 and has a similar diameter to bending region 101. The inner diameter of regions 102 or 103 may expand to a larger inner diameter from between about 0.001 to about 0.4 inches, preferably about 0.05 to about 0.35 inches, and most preferably between about 0.1 and about 0.3 inches.

Bending tool 10 may have an overall length from about 1 inch to about 7 inches, preferably about 2 to about 6 inches, and most preferably about 3 to about 5 inches. The length of the tool may be determined by the length of the medical device component to be bend, such that bending tool 10 is shorter than the component for ease of removal but long enough to impart the desired bend. The length of each flared insertion regions 102 or 103 may be from about 0.1 to about 1.5 inches, preferably from about 0.12 to about 1 inches, and most preferably from about 0.15 to about 0.5 inches. Each flared insertion region may have the same or different lengths and/or diameters.

Bending tool 10 may be used to bend various medical device components, such as needles, cannulas, dilators, trocar stylets, or the like. Bending tool 10 may also bend any hollow or tubular medical device component which can fit within bending tool 10.

The shape, size, location, and angle of a bend may be determined by a medical professional before bending. Typically, the bend will be near the distal end. The medical professional may use medical imaging techniques, such as fluoroscopy, x-ray radiography, magnetic resonance imaging, medical ultrasonography or ultrasound, endoscopy, elastography, tactile imaging, thermography, medical photography and nuclear medicine functional imaging techniques as positron emission tomography (PET) or Single-photon emission computed tomography (SPECT) to determine the bend required for a particular procedure and patient.

Figure 3A:
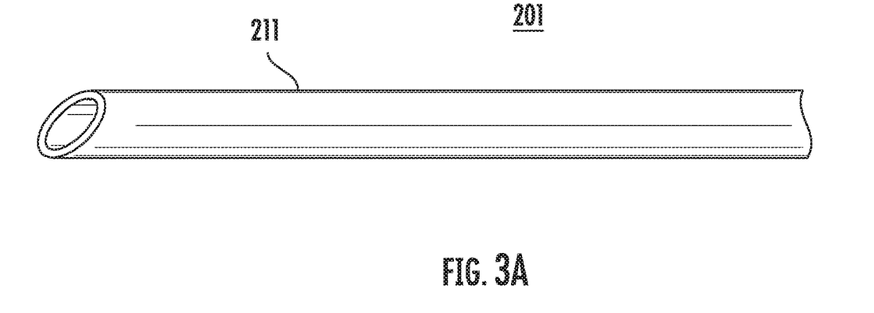
FIG. 3a is a view of a representative straight needle requiring bending for a medical procedure.
Figure 3B:
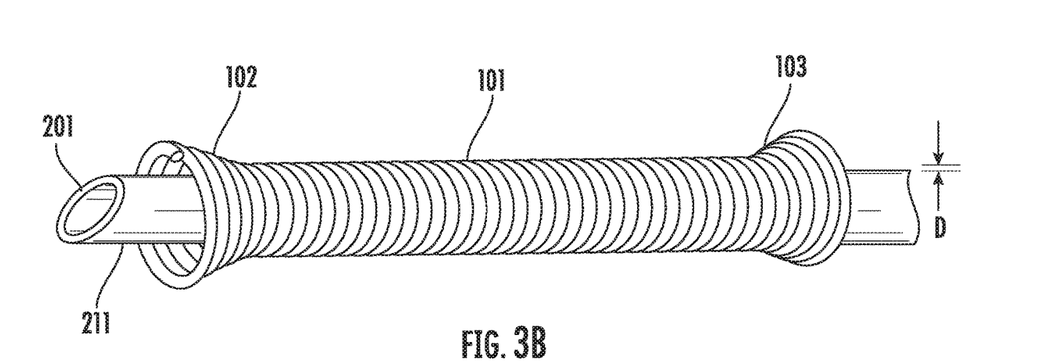
FIG. 3b is a view of a representative straight needle inserted into the bending tool of FIG. 1.

FIGS. 3a-3d illustrate possible steps of use of bending tool 10. As seen in FIG. 3a, straight puncture needle 201 is shown which requires a certain bend for a particular medical procedure. Puncture needle 201 is inserted into bending tool 10 as shown in FIG. 3b. If bending tool 10 includes one or more flared insertion regions 102 and/or 103, the insertion region aids with the insertion of needle 201 by guiding the leading tip of needle 201 in a decreasing diameter towards bending region 101.

Figure 3C:
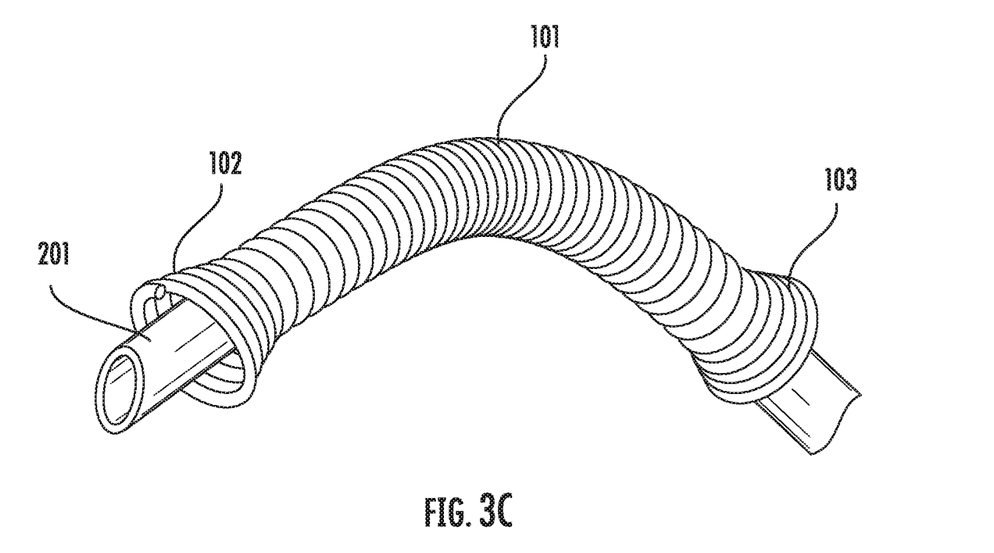
FIG. 3c is a view of the representative needle and bending tool of FIG. 3B after a bending process.

As shown in FIG. 3c, puncture needle 201 in inserted far enough into bending tool 10 such that the desired bend location on needle 201 is located within bending region 101 of bending tool 10. Bending tool 10 may be manually bent, causing needle 201 to bend simultaneously. During bending outer surface 211 of needle 201 may contact interior surface 110 of bending tool 10. The bending of bending tool 10 may be performed by abutting a portion of bending region 101 against a fulcrum (not shown). This fulcrum may be a user's fingers or thumbs or other object. The object may be sized appropriate to the size of the desired bend, such that as a user bends bending tool 10 around a fulcrum, it substantially bends to same shape of the fulcrum. In some instances, over bending is required to achieve the desired angle or curvature.

As needle 201 bends and undergoes plastic deformation, bending tool 10 forces needle 201 to bend while maintaining a similar cross section size, shape, and/or area to the unbent needle. Bending tool 10 prevents the diameter of the needle from changing substantially in any direction, as outer surface 211 of needle 201 is forced into place by interior surface 110 of bending tool 10. This ensures needle 201 maintains the same general cross sectional shape, size, and/or area so that, even after bending, the flow characteristics of needle 201 is minimally impacted. Furthermore, it prevents a kink from forming in needle 201 from bending by distributing the bending curve over a longer region of needle 201. Under ideal conditions, bending tool 10 may cause one side of needle 201 to stretch and the other side to compress, thus forming a bend or curve. Bending gap D3 describes the distance between outer surface 211 and inner surface 110. One may appreciate that minimizing D3 results in more effective bending action by minimizing deformation of the cross section of a bent component.

Bending tool 10 may be used in iterative stages to bend a medical device component. A user may use bending tool 10 to impart an initial bend, check the initial bend against a desired bend, and use bending tool 10 to change the initial bend or add another bend. Also, bending tool 10 can impart multiple bends into a medical device component without remove the component. Either by moving the fulcrum or by adjusting the position of the component within bending tool 10, multiple bends can be imparted into the component.

Figure 3D:
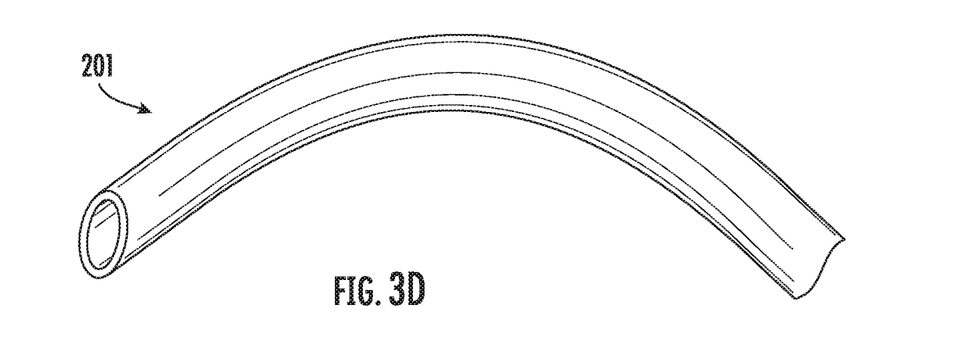
FIG. 3d is a view of representative needle of FIG. 3C after a bending process.

Lastly, as shown in FIG. 3d, bending tool 10 is slid off of puncture needle 201. Bending tool 10 may be twisted along its longest central axis to apply a torsional force to aid in removal of bending tool 10 by enlarging or shrinking the diameter of bending tool 10. As needle 201 has undergone plastic deformation, it substantially maintains the shape bent into it. Under ideal conditions, bending tool 10 has only undergone elastic deformation and will return to substantially the same configuration as it was prior to bending. Bending tool 10 may be designed as single use or as reusable.

Figure 4:
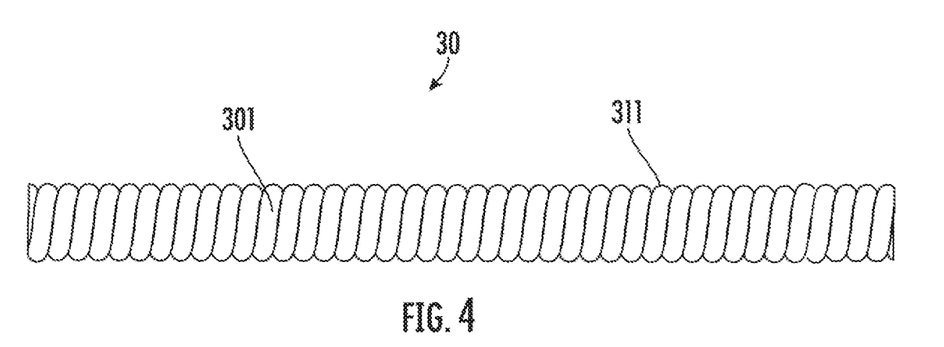
FIG. 4 is an orthogonal view of an alternative embodiment of the bending tool of FIG. 1.

One alternative embodiment of the present invention is shown in FIG. 4 as bending tool 30 with outer surface 311.

Bending tool 30 comprises a single bending region 301 with a substantially consistent diameter D2 along the entire length of bending tool 30. The outer surface 310 of bending tool 30 is formed by coils of wire. While bending tool 30 may be more difficult to use because it does not contain tapered insertion regions, it benefits from being easier to manufacture and package. Furthermore, it can be used both as an internal or external bending spring, i.e. a component can be inserted into bending tool 30 or bending tool 30 can be inserted into a component.

Figure 5A:
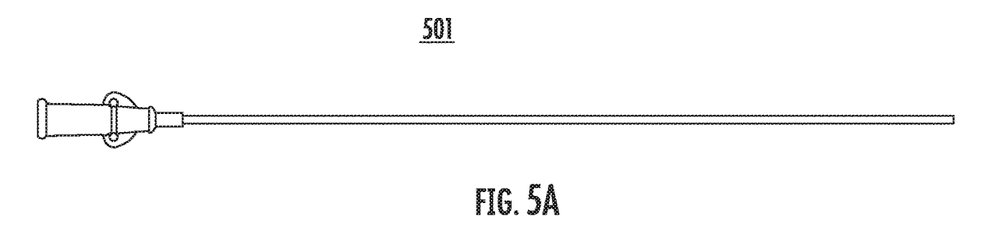
FIG. 5a shows a representative catheter which may be included in a kit with a bending tool.
Figure 5B:
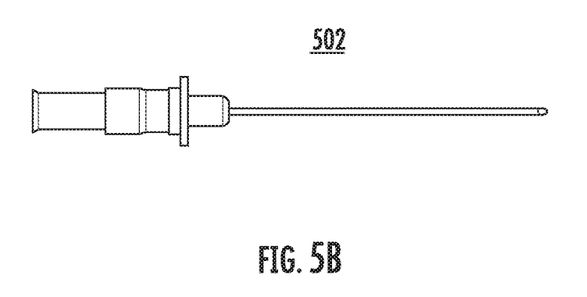
FIG. 5b shows a representative needle which may be included in a kit with a bending tool.
Figure 5C:
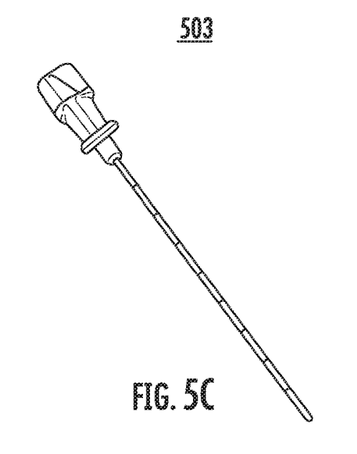
FIG. 5c shows a representative cannula which may be included in a kit with a bending tool.

Bending tool 10 may be bundled with other medical devices and/or components into one or more kits. The kit may include more than one bending tool 10 and each bending tool 10 may be a different size and/or configuration. A kit may also include one or more bending tools 10, 30 and/or 40. Bending tool 10 may be sized to bend one or more of the devices or components in the kit. These kits may include one or more of the following items: a catheter, needle, introducer sheath, sheath stiffener, trocar, cannula, dilator, or other medical devices or components. The kit may also include medical devices or components used in TIPS procedures, transjugular liver biopsy ("TLAB") procedures, or the like. A representative catheter is shown in FIG. 5a as catheter 501. A representative needle is shown in FIG. 5b as needle 502. A representative cannula is represented in FIG. 5c as cannula 503.

Catheter 501 may be a catheter used in TIPS, TLAB, or other medical procedures. Needle 502 may be a hypodermic, biopsy, intravenous, puncture, guide, Colapinto, or other kinds of needles used in medical procedures. Cannula 503 may be a venous, arterial or other kind of cannula.

Figure 6:
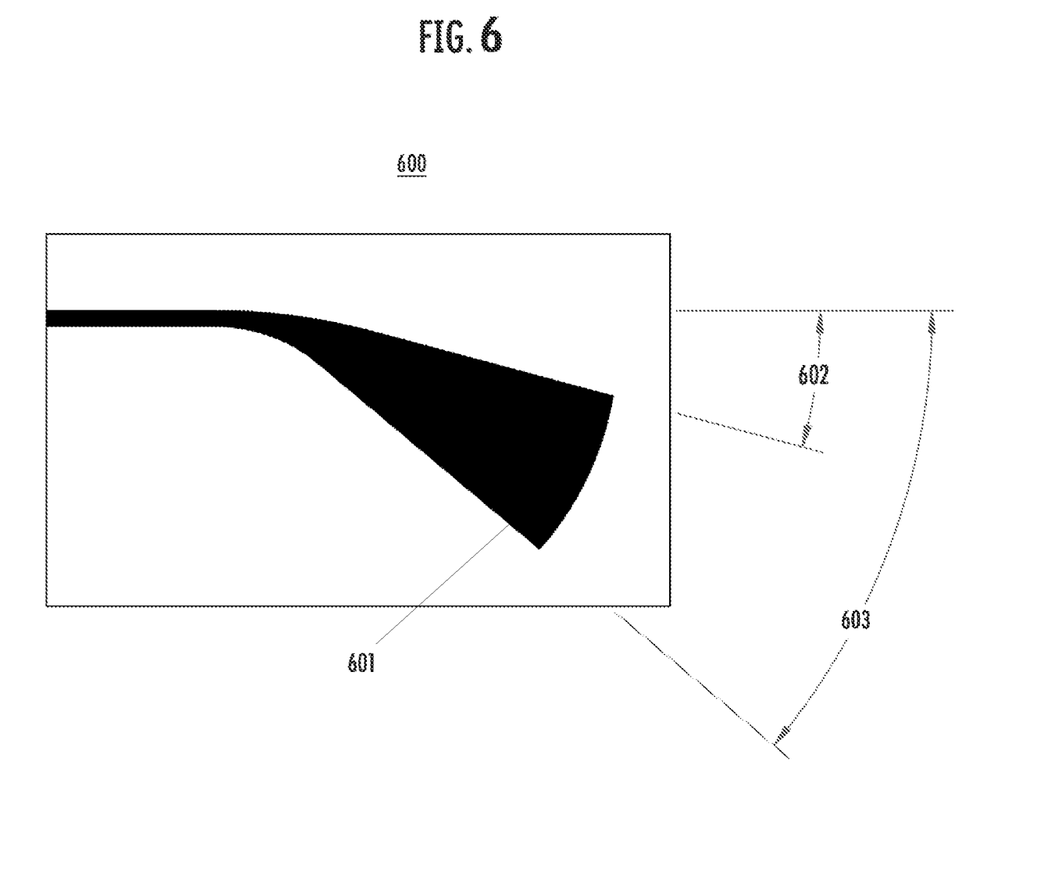
FIG. 6 shows an orthogonal view of a bending template.

As shown in FIG. 6, a kit may include one or more bending template 600 to assist the bending of a medical device component. Bending template 600 may include bending guide region 601 to show certain predetermined bending shapes, sizes, and angles. Bending template 600 may show an initial angle 602, showing the bending angle initially manufactured into a medical device component. Initial angle 602 may range from about 0 degrees to about 30 degrees and more preferably about 15 degrees. Bending template 600 may show maximum bending angle 603, wherein maximum angle 603 illustrates to a user the maximum angle a given medical device component can withstand before undergoing performance deterioration. Maximum angle 603 may range from about 0 degrees to about 90 degrees, more preferably about 40 degrees. Ideally, the final bent medical device component will have a bend angle between initial angle 602 and maximum angle 603.

Bending template 600 may comprise one or more lines, dots, marks, shaded regions, or the like on a sheet of paper, plastic, or the like. Bending template 600 may be printed on directions for use or a separate insert. Bending template also may be integrated into a product tray or container, either by printing, molding, stamping, or the like.

The kit may include directions for use. The directions for use may describe instructions for using bending tool 10. The directions for use may also describe directions for conducting a medical procedure with the items in the kit, such as a TIPS or TLAB procedure. The directions for use may include one or more embodiments of one or more sizes of bending template 600.

The foregoing disclosure and description of this invention are illustrative and explanatory thereof, and various changes in the size, shape, and materials as well as the details of the illustrated construction may be made without departing from the spirit of the invention.

The invention claimed is:

1. A method of bending a medical device component for use in a contemporaneous or shortly succeeding medical procedure, the method comprising:
   inserting the medical device component into a bending tool,
   bending the bending tool and the medical device component,
   removing the bent medical device component from the bending tool, and
   utilizing the bent medical device component in the medical procedure;
   wherein after the removing step, comparing the bent medical device component to a bending template and determining if the bent medical device is bent to a lesser angle than a maximum angle displayed on the bending template indicating that the user can bend the medical device component again if needed.

2. The method of claim 1 wherein:
   the bending tool is a bending spring.

3. The method of claim 1 wherein:
   the medical device component is selected from a group consisting of: a cannula, a catheter, and a needle.

4. The method of claim 1 further comprising:
   before the inserting step, determining a desired bend shape and location using a medical imaging technique.

5. The method of claim 1 further comprising:
   the bending tool comprises a steel alloy.

6. The method of claim 1 wherein:
   the medical procedure is a transjugular intrahepatic portosystemic shunt procedure.

7. The method of claim 1 further comprising:
   repeating the inserting, bending, removing, and comparing steps until a desired bend is achieved.

8. The method of claim 1 wherein:
   the bending tool comprises a helical coil of wire.

9. The method of claim 1 further comprising:
   after the bending step, the bending tool is twisted along a central axis to apply a torsional force to increase the distance between the bending tool and the medical device component, wherein the increased distance reduces friction between the medical device component and the bending tool, easing the removal of the component.

10. The method of claim 1 further comprising:
    prior to the bending step, placing a fulcrum at a desired bending location, and applying a first force and a second force generally opposite the location of the fulcrum, where the first force is spaced apart from the fulcrum towards a first end of the bending tool and the second force is spaced apart from the fulcrum towards a second end of the bending tool.

11. The method of claim 10 wherein:
    the fulcrum is a user's thumb.

12. The method of claim 1 wherein:
    the bending tool is adapted to fit a 14 gauge cannula.

13. The method if claim 1 wherein:
    the bending tool is adapted to fit a 16 gauge needle.

14. A method of producing a curve in a medical device component for use in a contemporaneous or shortly succeeding medical procedure comprising:
    embedding the medical device component into a bending tool,
    aligning an intended curve region of the medical device component within a bending region of the bending tool,
    producing a curve in the intended curve region of the medical device component, withdrawing the bent medical device component from the bending tool, and utilizing the bent medical device component in the medical procedure;

wherein prior to the producing a curve step, placing a fulcrum at the intended curve region of the medical device component, and applying a first force and a second force generally opposite the location of the fulcrum, where the first force is spaced apart from the fulcrum towards a first end of the bending tool and the second force is spaced apart from the fulcrum towards a second end of the bending tool.

* * * * *